United States Patent
Bruno et al.

(10) Patent No.: US 7,910,297 B2
(45) Date of Patent: Mar. 22, 2011

(54) THERAPEUTIC NUCLEIC ACID-3'-CONJUGATES

(75) Inventors: John G. Bruno, San Antonio, TX (US); Judson C. Miner, San Antonio, TX (US)

(73) Assignee: Operational Technologies Corporation, San Antonio, TX (US)

( * ) Notice: Subject to any disclaimer, the term of this patent is extended or adjusted under 35 U.S.C. 154(b) by 903 days.

(21) Appl. No.: 11/058,054

(22) Filed: Feb. 15, 2005

(65) Prior Publication Data

US 2005/0191680 A1 Sep. 1, 2005

Related U.S. Application Data

(60) Provisional application No. 60/548,629, filed on Feb. 27, 2004.

(51) Int. Cl.
*C12Q 1/68* (2006.01)
(52) U.S. Cl. ........... 435/6; 435/325; 435/375; 536/24.5; 536/24.31; 536/24.1
(58) Field of Classification Search .................. None
See application file for complete search history.

(56) References Cited

U.S. PATENT DOCUMENTS

| | | | |
|---|---|---|---|
| 5,270,163 A | | 12/1993 | Gold et al. |
| 5,475,096 A | | 12/1995 | Gold et al. |
| 5,573,913 A | * | 11/1996 | Rosemeyer et al. ............ 435/6 |
| 6,127,119 A | * | 10/2000 | Stephens et al. ................ 435/6 |
| 6,172,208 B1 | * | 1/2001 | Cook .......................... 536/23.1 |
| 6,235,886 B1 | * | 5/2001 | Manoharan et al. ......... 536/22.1 |
| 6,566,343 B2 | | 5/2003 | Biesecker et al. |
| 6,623,926 B1 | | 9/2003 | Lohse et al. |
| 6,780,850 B1 | | 8/2004 | Dougan et al. |

OTHER PUBLICATIONS

Petrie et al. An Improved CPG Support for the Synthesis of 3' amine-tailed oligonucleotides. Bioconjugate chem. 192, vol. 3: 85-87.*
Martin et al. Tailing and 3'-end labeling of RNA with yeast poly(a) polymerase and various nucleotides. RNA, 1998, vol. 4: 226-230.*
Bell, et al., "Oligonucleotide NX1838 Inhibits VEGF165-Mediated Cellular Responses In Vitro," In Vitro Cell Develop.Biol Animal. (1999) 35:533-542.
Biesecker, et al., "Derivation of RNA Aptamer Inhibitors of Human Complement C5," Immunopharm (1999) 42:219-230.
Blank, et al. "Systematic Evolution of a DNA Aptamer Binding to Rat Brain Tumor Microvessels, Selective Targeting of Endothelial Regulatory Protein Pigpen," J. Biol. Chem. (2001) 276:16464-16468.
Brody, E.N. and Gold, L., "Aptamers as Therapeutic and Diagnostic Agents," Reviews in Mol. Biotechnol. (2000), 74:5-13.
Bruno, In Vitro Selection of DNA to Chloroaromatics Using Magnetic Microbead-Based Affinity Separation and Fluorescence Detection, Biochem. Biophys. Res. Comm. (1997) 234: 117-120.
Bruno and Kiel, "In Vitro Selection of DNA Aptamers to Anthrax Spores with Electrochemiluminescence Detection," Biosensors & Bioelectronics (1999) 14:457-464.
Bruno and Kiel, "Use of Magnetic Beads in Selection and Detection of Biotoxin Aptamers by ECL and Enzymatic Methods,"BioTechniques (2002) 32:178-183.
Dougan, et al., "Extending the Lifetime of Anticoagulant Oligodeoxynucleotide Aptamers in Blood," Nuclear Med. Biol. (2000) 27:289-297.
Drolet, et al., "Pharmacokinetics and Safety of an Anti-Vascular Endothelial Growth Factor Aptamer (NX1838) Following Injection into the Vitreous Humor or Rhesus Monkeys," (2000) Pharm. Res. 17:1503-1510.
Hicke, et al., "Tenascin-C Aptamers are generated Using Tumor Cells and Purified Protein," J. Biol. Chem. (2001) 276:48644-48654.
Homann and Goringer, "Uptake and Intracellular Transport of RNA Aptamers in African Trypanosomes Suggest Therapeutic 'Piggy-Back' Approach," Bioorg. Med. Chem (2001) 9:2571-2580.
Huang, et al., "Highly Specific Antiangiogenic Therapy is Effective in Suppressing Growth of Experimental Wilms Tumors," J. Pediatric. Surg. (2001) 36:357-361.
Murphy, et al., "An Improved Method for the In Vitro Evolution of Aptamers and Applications in protein Detection and Purification," Nucleic Acids Res. (2003) 31:e110-e118.

(Continued)

*Primary Examiner* — Kimberly Chong
(74) *Attorney, Agent, or Firm* — Winstead PC

(57) ABSTRACT

Methods are described for improvement of the serum half life of therapeutic nucleic acids by 3' conjugation to useful target proteins, or other large molecules with useful function. In one embodiment, a 3' A, C or G overhang is added to ds-DNA and the primary amines conjugated using biocompatible bifunctional linkers to proteins. The resulting nucleic acid-3'-conjugates are serum nuclease-resistant and retained in vivo for long periods without rapid kidney clearance. Further, the choice of conjugate imparts additional functionality to the nucleic acid-3-conjugate.

Figure 1:
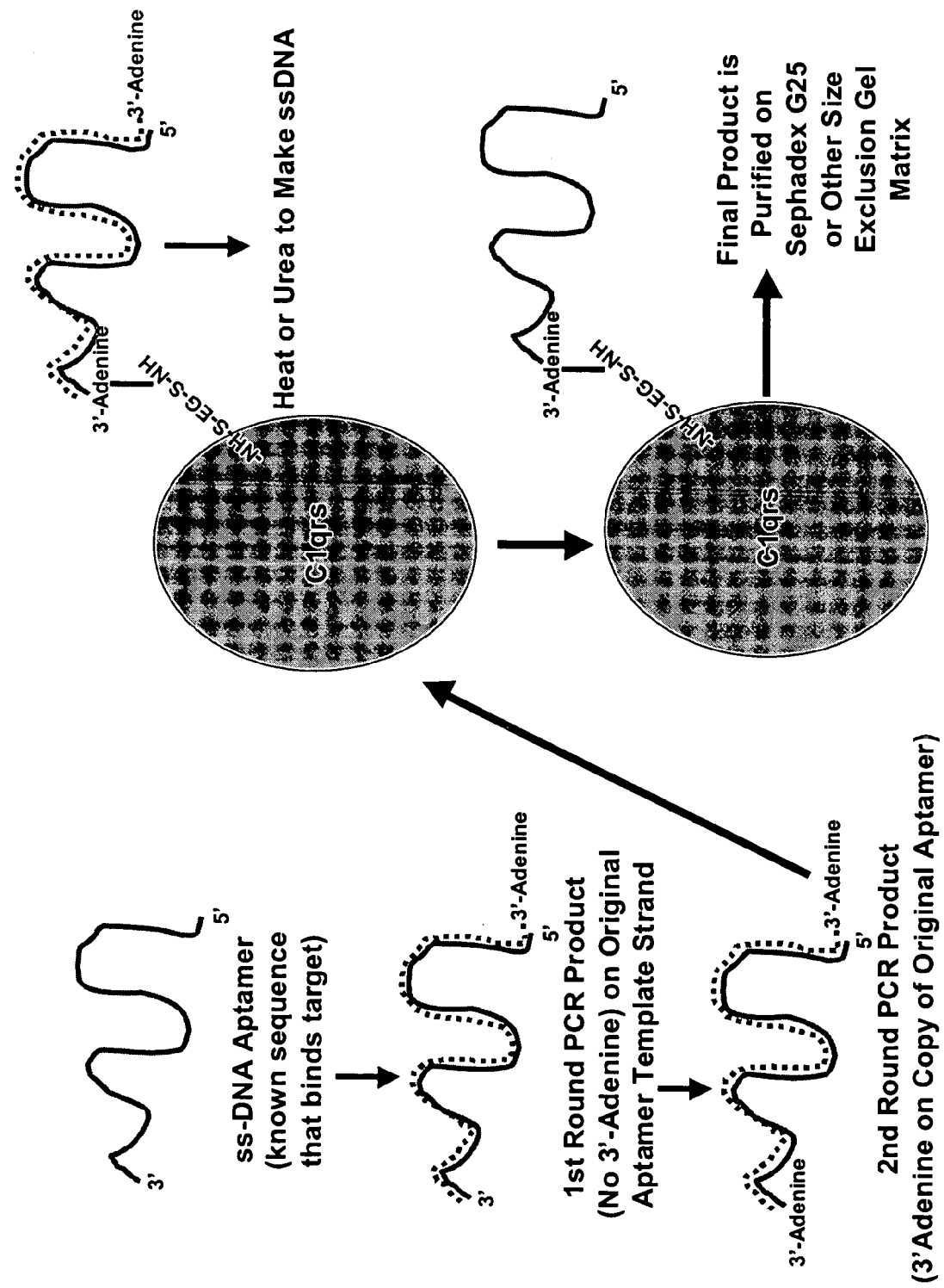
Figure 2:
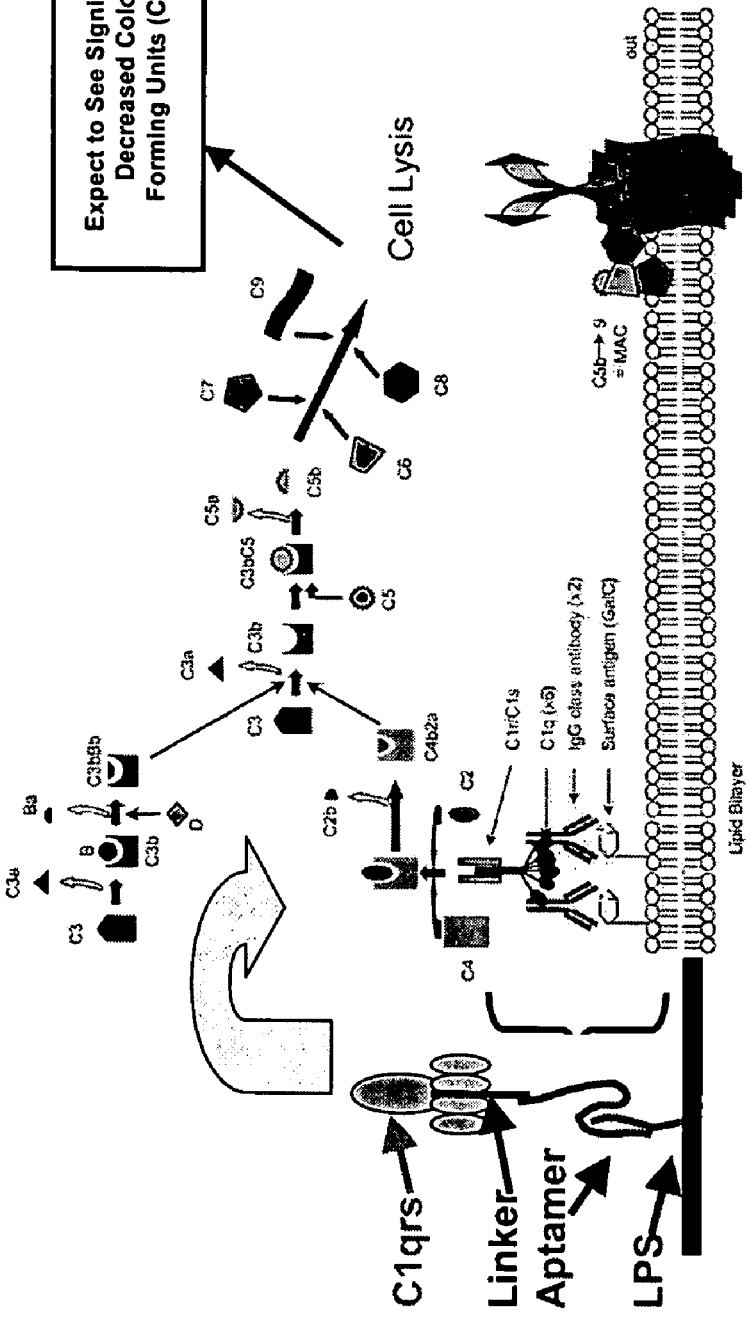

For example, if the protein in the DNA-protein conjugate is the first component of the complement cascade (C1q or C1qrs) and the DNA aptamer has been developed against surface components of a target cell, it can be used to treat bacterial or parasitic infections and cancers. If the protein is serum albumin or another common (nonimmunogenic) blood protein and the aptamer is directed against a toxin or venom, the aptamer-protein conjugate can be used as an antidote that binds and neutralizes the toxin or venom. Similar DNA (aptamer)-nanotube, -enzyme, and -toxin conjugates could also be used to target and selectively kill bacteria, parasites, and cancer cells in vivo. If the protein is an Fc antibody fragment or C3b protein from the complement system and the aptamer is developed against a bacterial cell capsular material, other cell surface component or viral cell surface component, then the aptamer-3'-protein conjugate can aid in opsonization of the target cells or viruses by phagocytic leukocytes.

4 Claims, 4 Drawing Sheets

OTHER PUBLICATIONS

Ono, T, et al.,"2'-Fluoro Modified Nucleic Acids: Polymerase-Directed Synthesis, Properties and Stability to Analysis by Matrix Assisted Laser Desorption/Ionization Mass Spectrometry," Nucl. Acids Res. (1997), 25:4581-4588.

Ruckman, J., et al., "2'-Fluropyrimidine RNA-Based Aptamers to the 165 Amino Acid Form of Vascular Endothelial Growth Factor ($VEGF_{165}$)," J. Biol. Chem. (1998) 273:20556-20567.

Ulrich, et al., "In Vitro Selection of RNA Aptamers that Bind the Cell Adhesion Receptors of *Trypanosoma cruzi* and inhibit cell invasion," J. Biol. Chem. (2002) 277:20756-20762.

Welkos, et al., "The Role of Antibodies to *Bacillus Anthracis* and Anthrax toxin components in Inhibiting the Early Stages of Infection of Anthrax Spores," Microbiology (2001), 147:1677-1685.

Chu, Ted C., et al; Aptamer: Toxin Conjugates That Specifically Target Prostate Tumor Cells; Cancer Research; Jun. 15, 2006; pp. 5989-5992; 66(12); Am. Association for Cancer Research; Austin, TX , US.

Abe, Ikuro, et al; Enzymatic formation of unnatural cytokinin analogs by adenylate isopentenyltransferase from mulberry; Science Direct; Feb. 15, 2007; pp. 795-800; Biochemical and Biophysical Research Communications 355; www.elsevier.com/locate/ybbrc.

Zahler, Alan M., et al.; Telomere terminal transferase activity in the hypotrichous ciliate Oxytricha nova and a model for replication of the ends of linear DNA molecules; Nucleic Acids Research;1988; pp. 6953-6972; IRL Press Ltd.; Oxford, England.

* cited by examiner

THERAPEUTIC NUCLEIC ACID-3'-CONJUGATES

PRIOR RELATED APPLICATIONS

This patent application claims priority to U.S. Provisional Application Ser. No. 60/548,629, filed on Feb. 27, 2004, the disclosure of which is incorporated by reference in its entirety herein.

STATEMENT OF GOVERNMENT SPONSORED RESEARCH

At least a portion of this invention was funded by SBIR contract number DMI-0319766.

FIELD OF THE INVENTION

The present invention relates to the field of nucleic acid-based therapeutics where nucleic acid stability and retention are improved by a 3' conjugation to a therapeutic protein. More specifically, the present invention relates to methods for production of aptamers, antisense and other nucleic acid based therapeutics that are blocked at their 3' ends with a protein, or other large macromolecule such as a nanotube or biocide. The 3' blocked nucleic acids have surprisingly increased stability, increased retention in the body, and with the judicious selection of conjugate can have additional therapeutic benefit as well.

For example, the therapeutic nucleic acid, such as an aptamer can be conjugated to a biocidal protein. Thus, the aptamer functions to selectively deliver the biocide to the desired target, such as a bacteria, virus or cancer cell, which is then killed by the biocide. Similarly, nanotubes can effect the delivery of small molecule drugs contained by the lattice structure of the nanotube or ball.

BACKGROUND OF THE INVENTION

Aptamers, derived from the latin aptus, meaning, 'to fit', are oligonucleotides that have a specific three dimensional shape and consequent biological activity. Aptamers are generally produced through a process named "systematic evolution of ligands by exponential enrichment" or "SELEX," which is an iterative selection and amplification process. Nucleic acids that bind to a target are selected (non-binders are simply washed away) and then subjected to a round of amplification. As this process is iterated, tightly binding aptamers are enriched in the population, and extremely tight and specific binding between the aptamer and the target can be achieved. The reader is referred to U.S. Pat. No. 5,270,163 and the very large family of related patents for detailed SELEX protocols.

The extraordinary capacity of aptamers to bind tightly to specific targets underlines their tremendous potential as molecular therapeutics. For example, aptamers can be used to selectively target cells (such as tumor cells or pathogens) for death.

For example, U.S. Pat. No. 6,566,343 discusses the potential for aptamers directed at cell surface components of bacteria, cancer cells and parasites to activate the complement system and bring about the lysis of target cells. The patent discloses the linkage of two aptamers—one directed against the target cell and a second one against a component of the complement system (thus recruiting the complement cascade to the target cell)—to achieve complement activation and targeted cell death.

There are two distinct disadvantages to this approach. First, the aptamer-aptamer conjugates are subject to degradation from serum nucleases and second, the aptamer-aptamer conjugates are subject to rapid clearance by the kidneys. Thus, although aptamers are a powerful targeting system, in vivo nucleic acid stability remains a problem.

A Canadian team of researchers (Dougan et al., 2000) demonstrated that 3'-biotinylation of DNA significantly increased its resistance to serum nuclease activity. This was presumably due to steric hindrance and suggests that any 3' or 5' capping or nucleic acid modification should improve nucleic acid stability in vivo.

However, our research surprisingly indicates that 5'-biotinylation is not very effective against serum degradation of DNA, nor is the incorporation of 2'-Fluoro modified deoxynucleotide triphosphates (2'F-dNTPs). Thus, the stability issue is not as simply addressed as one might predict. Hence, improved methods of stabilizing nucleic acids for in vivo therapeutic use are still needed and the invention addresses this problem.

BRIEF SUMMARY OF THE INVENTION

The invention presents a novel means to conjugate nucleic acid at its 3' end to proteins or other large macromolecules (e.g., polyethylene glycols, nanotubes, and the like). The 3' conjugation inhibits the action of serum nucleases that would otherwise rapidly breakdown the DNA in blood, and it dramatically increases retention of the aptamers in blood, which would otherwise be rapidly filtered out by the kidneys.

The invention allows the production of aptamers, antisense and other nucleic acid based therapeutics that are blocked at their 3' ends with therapeutic proteins and therapeutic uses for the nucleic acid-3'-conjugates. Generally speaking, ds-DNA is conjugated at its 3' end, followed by conversion to single strand (ss) DNA-3'-conjugates. The 3' conjugates show remarkable serum nuclease resistance and retention in the body and exhibit enhanced therapeutic efficacy as compared with same DNA in a naked (unconjugated) form.

The conjugation requires the addition of adenine (A), cytosine (C), or guanine (G) to the 3' end of double strand (ds) DNA by means of various enzymes (thymine has no free primary amine group). In particular, *Thermus aquaticus* (Taq) DNA polymerase adds a 3'-A overhang during the PCR process and the template independent enzyme terminal deoxynucleotide transferase (TdT) can add A, C, or G to the 3' end of blunt ended ds-DNA, if only A, C, and G are supplied (i.e., no thymine is provided). With TdT, the undesired complementary strand will become conjugated to the protein as well, but it will be nonfunctional and nonallergenic, because DNA is of low immunogenicity.

Free primary amines in the terminal A, C, or G's can then be used to link the DNA to a protein (or other conjugate) via a bifunctional linker with an N-hydroxy-succinimide or other suitable functionality. The conjugate is specifically added to the 3' overhang because the remainder of the DNA molecule is double-stranded and cannot participate in conjugation.

After conjugation, the ds-DNA is converted to ss-DNA by means of heating beyond the DNA's melting temperature ($T_m$) for a brief period. Care should be taken to avoid protein denaturation during the melting step. Melting is followed by purification of the ss-DNA-3'-conjugate by chromatographic or other physical and chemical means including affinity separation methods, differential or density centrifugation, and preparative electrophoresis.

Such aptamer-3'-conjugates have a variety of applications. A key application is the targeted killing of pathogens or tumor cells. For example, if the protein conjugate is human or animal Clqrs (or some portion of the complex) it will activate the complement cascade as shown herein, thus targeting the cell for destruction by the immune system. The Clqrs is delivered to the target cell by virtue of being coupled to an aptamer specific for that cell.

Alternatively, one can couple aptamers to carbon nanotubes or other types of nanotubes to bind the surface of an undesirable target cell and kill it by puncturing the cell membrane or cell wall with the attached nanotube. To be effective at killing, aptamer-3'-nanotube conjugates would require energy input via a molecular motor driven by adenosine triphosphate (ATP), creatine phosphate, or other innovative means of energetically driving the nanotube into the target cell membrane to puncture and lyse the target cell.

Another key application of aptamer-3'-conjugates would be neutralization of toxins (e.g., botulinum toxins, cholera and diphtheria toxins, digitalis, ricin, staphylococcal enterotoxins, etc.) by use of specifically developed ss-aptamers linked to serum albumin (SA) to prevent aptamer breakdown and clearance from the blood. The aptamer-3'-SA binds tightly to the toxin, thus neutralizing its effect.

Coupling of aptamers to the complement system could be advantageous in the killing of antibiotic-resistant bacteria, cancer cells, parasites and other target cells. Carbon nanotubes, toxins, and destructive enzymes might also be coupled to the 3'-end of aptamers to create highly effective and long-lived therapeutics against invading cells or target cells.

BRIEF DESCRIPTION OF THE DRAWINGS

FIG. 1 shows a schematic of the process for conjugation of a known DNA aptamer sequence at its 3' end to an effector protein of choice (in this example, Clqrs to activate the complement cascade).

FIG. 2 shows the theoretical aptamer-3'-Clqrs conjugate bacterial killing mechanism. In the figure, IgG antibodies are replaced by the aptamer-3'-Clqrs conjugate and activate the Classical complement cascade. Lipopolysaccharide (LPS) is shown as a target surface antigen for Gram negative bacteria, but LPS could be replaced by any bacterial cell surface component that is accessible.

FIG. 3 illustrates how an aptamer can be used to inhibit or inactivate a toxin, such a botulinum toxin. The aptamer-3'-protein conjugate is not shown in this figure, but human serum albumin would be a good candidate for such conjugation to ensure no allergic reaction in human patients. The figure shows botulinum toxin as an example and illustrates binding and inhibition of the holotoxin and the 50 kiloDalton zinc endopeptidase subunit, which is enzymatically active on the SNAP25 peptide in neurons and is used as the basis for a fluorescence resonance energy transfer (FRET) assay known as the SNAPtide™ assay.

FIG. 4 shows clear inhibition (decreased light levels) of botulinum toxin serotype A (BoNT A) by DNA aptamers developed against BoNT A holotoxin (panel A) and the 50 kD zinc endopeptidase subunit (panel B) using the SNAPtide™ FRET assay. In the SNAPtide™ FRET assay, the greater the fluorescence intensity, the greater the BoNT A activity, because more SNAP 25 FRET substrate is cleaved.

DETAILED DESCRIPTION OF THE INVENTION

The following examples are illustrative of various embodiments the invention and are not intended to be limiting. For example, we have exemplified the invention using aptamers, but it is equally applicable to antisense, ribozymes, gene therapy, and other therapeutic nucleic acids. Additionally, we have added the 3'-conjugate using the free primary amine of A, C, or G, which is a convenient means of specifically conjugating the 3' end, but other means of conjugation to the 3' end can be used. For example, the free carbonyl on G, T, C and U, can be used. Alternatively, a modified nucleotide equipped with target moieties for conjugation can be added as the 3' overhang. The diol on the 3'-ribose residue of RNA may be oxidized to result in two aldehyde groups using sodium meta-periodate and the aldehydes then can be conjugated to the amine groups on a protein using reductive amination with sodium cyanoborohydride. Nucleic acid conjugation techniques are well known in the art and need not be further detailed herein.

In the examples given herein, the bifunctional linker SULFO-EGS™ (PIERCE CHEMICAL CO.™) was used to couple the free primary amine from adenine to a protein conjugate. However, any biocompatible, nonallergenic, bifunctional linker could be used including EDP=3-[(2-aminoethyl)dithio]propionic acid; BMPH=N-[beta-maleimidopropionic acid]hydrazide; BMPS N-[beta-maleimidopropyloxy]succinimide ester; SULFO-DST=disulfosuccinimidyl tartrate; SULFO-EMCS=N-[epsilon-maleimidocaproyloxy]sulfosuccinimide ester.

Additionally, we have exemplified the invention using a protein conjugate, because such conjugates significantly improve the efficacy of the invention by conferring the activity of the protein to the therapeutic nucleic acid. However, experiments are planned to broaden the inventions application to include nanotubes or other large macromolecules with desirable properties. All that is required of the conjugate is that it be large enough to prevent the nucleic acid-3'-conjugates from being rapidly cleared by the kidneys, and that it protect the nucleic acid from degradation, without the conjugation adversely affecting the activity of either component.

Where the conjugate has biocidal activity, the nucleic acid-3'-conjugate can be used to selectively target and kill pathogens or cancer cells. Biocides include toxic proteins such as peptide toxin mellitin, peroxidase, TNF-alpha, *Bacillus thuringensis* crystal (cry) proteins, and the like; proteins that recruit the natural cell killing mechanisms, such as Clprs, Fc, C3b, C4b, C5a, and C567; phage lysis proteins, such as the SPO1 genes 40, 50 and 51; chemicals such as polystyrenes, eugenol, thymol, trichlorocarbanalide (TCC), didecyldimethylammonium chloride (DDDMAC) and C10-16-alkyldimethyl, N-oxides (ADMAO), Pentachlorophenol (PCP), and nanotobes containing small molecule drugs, such as antibiotics, or when used as a pore to penetrate target cells.

Other conjugates are designed merely to protect the therapeutic nucleic acid from degradation and retain its activity in the bloodstream, such as serum albumin (SA), human serum albumin (HSA), alpha1 and alpha2 globulins, beta-globulins, gamma-globulins, hemoglobin, and the like. Other conjugates can include antibodies or antibody fragments, designed to recruit other proteins or cell types to the therapeutic nucleic acid. These are particular useful in gene therapy techniques, such as suicide gene therapy or rescue gene therapy, where particular cells are to be targeted with a cytotoxic or functional gene.

Example 1

Nucleic Acid-3'-Protein Conjugation

Two prime (2') modifications of nucleotides in RNA aptamers have been reported to work well for nuclease resistance (Bell et al., 1999 and Ulrich et al., 2002) against certain specific bacterial nucleases and against serum nucleases. Some researchers claim that DNA aptamers can be protected by 2'-Fluoro-deoxynucleotide (dNTP) incorporation (Ono et al., 1997). However, there is not much definitive data on this topic in the literature. Further, it is difficult to incorporate 2'F-dNTPs into DNA by PCR (Ono et al., 1997) or other means as most DNA polymerases either will not incorporate 2'F-dNTPs (i.e., reject them as substrates or they are poorly incorporated) or the 2'-F-dNTPs are excised by the polymerase's editing function.

An alternative method for conferring resistance to serum nucleases is capping of the DNA termini, especially the 3' end as shown by Dougan et al. (2000). Dougan capped aptamers with the small molecule biotin and successfully preserved the aptamers in serum. However, we theorized that a larger peptide or protein could be conjugated to the 3' end of the aptamer with the added benefits of increasing aptamer retention in the blood (i.e., decreasing clearance by the kidneys, because the low molecular weight aptamer is attached to a large protein that cannot be filtered by the kidneys). In addition, a protein conjugate would provide the benefit of adding the functionality of the protein conjugate to the aptamer. The latter advantage can then be used for adding a wide variety of functions such as biocidal activity, enzymatic activity, enhancing phagocytosis (opsonization), cell recruitment or cell activation, or serum stability. It remained to be proven, however, that aptamer function and protein function could be retained when coupled together.

The goal of the process shown schematically in FIG. 1 was to terminate the aptamer in a deoxynucleotide containing a free amine group at the 3' end to enable covalent coupling to the protein conjugate. The aptamer may or may not have a free 3' amine group originally, but conjugation of a single-stranded aptamer would surely lead to a family of conjugates at different positions on the aptamer and no guarantee of serum nuclease resistance, or retention of aptamer activity. Hence, the aptamer was subjected to a round of the polymerase chain reaction (PCR) to create a complementary strand (dotted line) and a 3'-adenine (A) overhang that has a free amine moiety.

This 3'-A overhang was on the complementary strand, not on the desired aptamer strand. Therefore at least one more round of PCR was required to place the 3'-A overhang on the original template strand (solid line) and enable conjugation to the protein conjugate by means of a common bifunctional linker such as SULFO-EGS™ (ethylene glycol-bis (sulfosuccinimidylsuccinate)).

Once the aptamer was conjugated to a given protein at its 3' end, the double strand was melted by means of heating, which may denature the protein if the temperature is too high for an extended period of time, or by way of mild chemical treatments such as low concentrations of urea, which could again denature the protein if the concentration is too high. Other means of separating ds-DNA include the use of biological tools, such as SSB (Single-stranded DNA Binding Protein).

Finally, the single-stranded aptamers and the aptamer-3'-protein conjugates can be separated by a variety of physical means such as size exclusion gel chromatography on materials such as Sephadex, density gradient centrifugation, or preparative electrophoresis, etc. The aptamer-3'-conjugate can also be separated by affinity chromatography using an antibody against the protein conjugate, and this system can be coupled with mild denaturation, thus allowing purification and separation in a combined step.

Bruno (1997) and Bruno and Kiel (2002) as well as Murphy et al. (2003) have described a method for immobilizing target molecules onto magnetic microbeads (MBs) and using these target-MBs to magnetically separate out aptamers from a randomized oligonucleotide library which bind the target with high affinity. Then using standard SELEX techniques (Bruno and Kiel 2002), a family of aptamers can be selected that will bind the target with high affinity and can be conjugated at their 3' ends by way of the process shown in FIG. 1.

Example 2

Aptamer-3'-LPS

Sulfo-EGS was dissolved at 10 mg/mL in sterile PBS and 132 μL of this stock solution added to 0.1 mg of human C1qrs protein (molecular weight of 750 kD). This ratio provided the 20-fold molar excess of Sulfo-EGS recommended for Sulfo-EGS conjugations.

One hundred μL (approximately 33 μg) of SELEX round 5 or greater DNA aptamers in their cold (double-stranded) form was added to the solution. The reactants were allowed to stand at RT for 1 hour and were then added to a PHARMACIA™ PD-10 desalting column (SEPHADEX™ G-25) equilibrated with several void volumes of sterile PBS. Twelve to fifteen 1 mL fractions were eluted in PBS and collected as individual fractions. Absorbance readings were taken for all fractions at 260 nm and 280 nm. In addition, 5 μL of each fraction was added to 5 μL of native polyacrylamide gel electrophoresis (PAGE) loading buffer and run on 8-10% polyacrylamide gels that were fixed and silver stained to verify successful conjugation.

The following steps were performed for *E. coli* O111:K58 (B4):H— (ATCC No. 33780) killing experiments. Twenty tryptic soy agar (TSA) petri plates were warmed to RT and labeled to represent four groups of five plates each. The five plates cover arbitrary *E. coli* ten-fold dilutions from $10^{-4}$ to $10^{-8}$ where the aptamer-C1qrs conjugates "antibiotic" effect was anticipated. One loopful of freshly cultured *E. coli* O111:K58(B4):H— (i.e., grown overnight at 35° C. on TSA agar) was added to 1 mL of Gelatin Veronal Buffer (GVB; SIGMA-ALDRICH CO.™, St. Louis, Mo.) at RT. Clumps were broken up by use of a 5 mL syringe and 20 gauge needle that was used to vigorously eject the bacterial sample ten times to achieve a uniform single cell suspension, as confirmed by phase-contrast microscopy at 400× magnification.

This stock bacterial suspension was used to make eight ten-fold dilutions in sterile polypropylene tubes. Both the stock bacterial suspension and nascent dilution were thoroughly mixed throughout the experiments to ensure random sampling. Fifty μL of each bacterial dilution was added to four other polypropylene microfuge tubes (representing the four treatment groups for each specified dilution of interest).

Ten μL of human serum complement proteins (SIGMA-ALDRICH™ #S-1764) diluted 1:500 (to avoid activation of the alternate complement pathway by LPS) in GVB was added to each tube in Groups 1 and 2.

One hundred μL of the aptamer-3'-C1qrs conjugate was added to five separate PCR tubes, and all were heated at 80° C. in the thermal cycler block for 5 minutes to make the anti-LPS aptamer portion of the conjugate single-stranded (Tm of the 60 mer was 78.5° C.). This temperature and duration did not appear to cause damage to the C1qrs part of the conjugate, because it still appeared to initiate bacterial killing, as shown below.

Fifty μL of the hot aptamer-C1qrs conjugate was added to Groups 1 and 4 of each killing experiment (50 μL×10 tubes=500 μL). Total volume of all tubes was equalized to 110 μL by addition of GVB as appropriate. Tubes were capped, shaken ten times, and incubated at 35° C. for 2 hours.

The tubes were decanted onto the TSA plates and the contents spread. Plates were placed face up at RT for 30 minutes and then inverted and incubated overnight at 35° C. The following day, plate counts were obtained and all plates were photographed.

It is well known that LPS from *E. coli* and other Gram negative bacteria can activate the complement cascade by the Alternate pathway. To eliminate or minimize the Alternate pathway of complement activation, a series of dilutions containing only human serum complement protein (HSCP) were added to the test bacteria to determine the lowest concentration (i.e., highest dilution) of HSCPs that did not kill significant numbers of *E. coli* bacteria by the Alternate pathway after a two hour incubation at 35° C. The results of the HSCP dilution experiment are given in Table 1 and indicate that between a 1:800 to 1:500 dilution of the HSCPs was appropriate for use in the later killing experiments, since that is where the killing effect of HSCP itself becomes apparent (i.e., significantly fewer than 300 colonies were seen per plate).

TABLE 1

Colony Counts of *E. coli* O111:B4 as a Function of HSCP Dilution
Colony Forming Units (cfu)

| HSCP Dilution | Trial 1 | Trial 2 |
|---|---|---|
| 1:10,000 | >300 | >300 |
| 1:1,000 | 287 | 283 |
| 1:800 | 241 | 238 |
| 1:500 | 187 | 172 |
| 1:400 | 98 | 90 |
| 1:200 | 57 | 63 |
| 1:100 | 18 | 21 |

Note: An arbitrary $10^{-4}$ dilution of *E. coli* was used. Grey indicates that at those dilutions there was sufficient complement to begin activating the alternate pathway of cell killing.

The aptamer-3'-C1qrs-mediated killing experiments contained four treatment groups as follows:

Group 1: Full Test Group—Contained 50 µL of the bacterial dilution plus 50 µL of anti-LPS aptamer-C1qrs conjugate and 10 µL of 1:500 dilution of HSCPs per tube.

Group 2: Control for Alternate Pathway Activation—Contained 50 µL of bacterial dilution and 10 µof 1:500 dilution of HSCPs plus 50 µL GVB per tube.

Group 3: Bacterial Growth Control—No chemical additives. This group indicates baseline growth levels of the bacteria. The group contained only 50 µL bacterial dilution and 60 µL of GVB per tube.

Group 4: Aptamer-C1qrs Conjugate Control—Contained only 50 µL of bacterial suspension plus 50 µL of aptamer-C1qrs conjugate and 10 µL of GVB (no HSCPs added, therefore the remainder of the complement cascade should not be present).

In the three aptamer-C1qrs bacterial killing experiments (Table 2), it became clear that, at certain higher dilutions, Groups 1 and 4 consistently showed fewer colonies than Groups 2 and 3. If the classical pathway of complement activation was being invoked by the anti-LPS aptamer-C1qrs conjugate, then one would predict a significantly lower number of colonies in Group 1. However, the lower number of colonies in Group 4 (conjugate only group) is somewhat perplexing. One possible explanation of the lowered colony numbers in Group 4 is that traces or residues of the other complement proteins (HSCPs) are present in the aptamer-C1qrs conjugate preparation and synergize with the conjugate to bring about elevated levels of bacterial killing. If that is not the case, then the aptamer-C1qrs conjugate may be able to kill bacteria by an unknown alternate mechanism that does not involve invoking the action of the complement cascade.

TABLE 2

Colony Counts from Three *E. coli* Aptamer-C1qrs Killing Experiments

| Group | Dilution | | | | |
|---|---|---|---|---|---|
| | 10e−4 | 10e−5 | 10e−6 | 10e−7 | 10e−8 |
| Experiment 1 | | | | | |
| 1 | TNTC | TNTC | 1 | 0 | 1 |
| 2 | TNTC | TNTC | 267 | 16 | 3 |
| 3 | TNTC | TNTC | 265 | 15 | 2 |
| 4 | TNTC | TNTC | 132 | 5 | 1 |
| Experiment 2 | | | | | |
| 1 | TNTC | TNTC | 141 | 13 | 0 |
| 2 | TNTC | TNTC | TNTC | TNTC | 207 |
| 3 | TNTC | TNTC | TNTC | TNTC | 216 |
| 4 | TNTC | TNTC | TNTC | TNTC | 67 |
| Experiment 3 | | | | | |
| 1 | TNTC | 199 | 34 | 4 | 0 |
| 2 | TNTC | TNTC | 167 | 55 | 2 |
| 3 | TNTC | TNTC | 155 | 74 | 3 |
| 4 | TNTC | 212 | 32 | 7 | 0 |

Note:
TNTC = Too Numerous to Count

Example 3

Antitoxin Aptamer-3'-HSA

Figure 3:
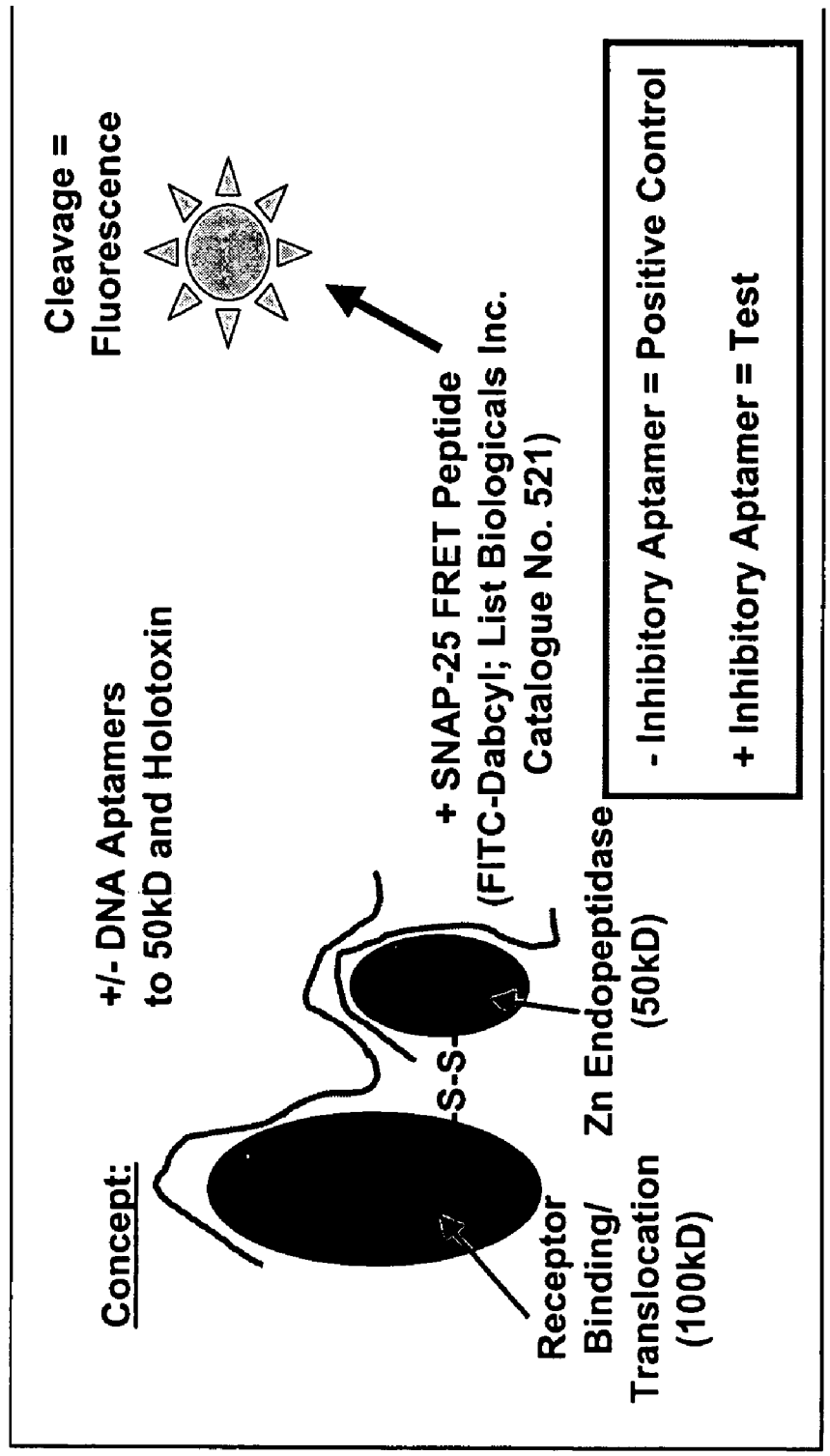

FIG. 3 illustrates the general concept of aptamer (or aptamer-3'-protein conjugate) binding to toxins to inhibit or inactivate the toxin. If the toxin is a small molecule that is inherently toxic to biological systems, then the binding of target-specific developed aptamers should ameliorate or eliminate toxicity by stoichiometrically wrapping around the toxin to disallow it from interacting within a biological system. If the toxin is an enzyme, then binding of a specific aptamer or aptamer-3'-protein (albumin) conjugate to the active site should diminish or cease enzymatic activity.

Figure 4:
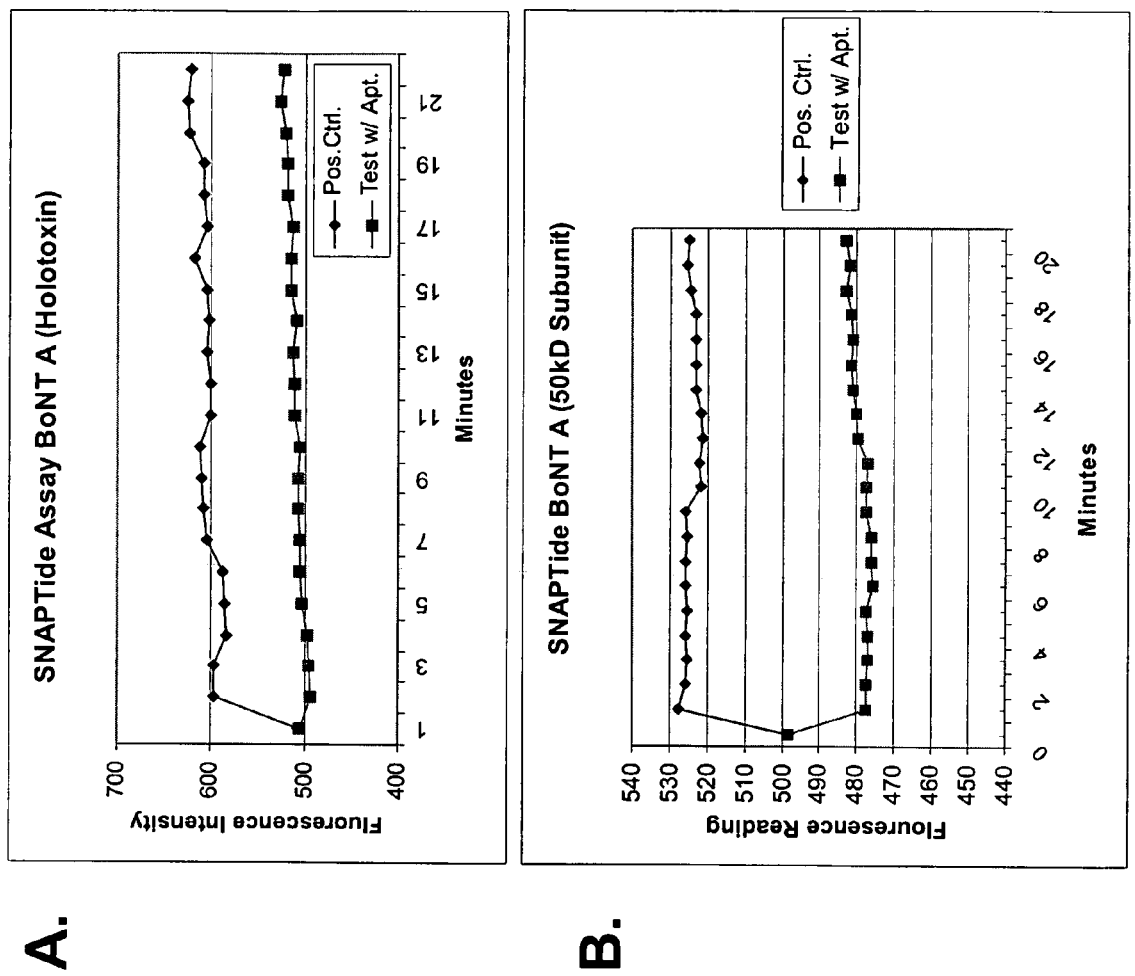

One example of DNA aptamer-mediated enzymatic toxin inhibition can be seen in the binding of specific botulinum A toxin (BoNT A) aptamers to BoNT A, thereby inhibiting the toxin's ability to cleave its SNAP 25 peptide substrate. Using a specific SNAP 25 FRET assay known as the SNAPtide™ assay, aptamers developed against both the holotoxin and the 50 kD zinc endopeptidase subunit of BoNT A showed evidence of significant toxin inhibition as seen in FIG. 4. Thus, it is shown that conjugation to a protein did not decrease either the aptamer or the protein conjugate's activity.

The SNAPtide™ assay procedure and buffer formulations are given here. 100 mL of Buffers A and B were made in nuclease-free sterile water according to Table 3 below. The pH was adjusted to 8.0 with strong base or acid, as needed, and the solutions filter sterilized and stored in a refrigerator, but warmed to RT before use.

A SNAPtide™ vial (fluorescein/dabcyl labeled peptide; LIST BIOL. LABS,™ No. 521) was reconstituted in 80 µL of DMSO to a stock concentration of 2.5 mM. 10 µL of Bot A (10 µg/mL) was preincubated in 190 µL of Buffer A (see composition below) at 37° C. for 30 minutes to activate the toxin.

10 µL of round 5 anti-BoNT A aptamers was added to 90 µL of Buffer B, mixed and preheated to 95° C. for at least 5 minutes in a closed Eppendorf tube under a vented chemical or biological hood.

Hot aptamer solution (100 μL) was added to 100 μL of activated BoNT A in an Eppendorf tube and allowed to bind at 37° C. for 15 minutes. This tube was labeled "Test." Similarly, 100 μL of Buffer B was added to 100 μL of activated BoNT A labeled "Control" and incubated at 37° C. for 10 minutes.

3 μL of stock SNAPtide™ (SNAP 25 FRET peptide fragment) were added to both tubes along with 2.7 mL of Buffer B. The contents of the tubes (3 mL each) were transferred to separate 10 mm methacrylate cuvettes and readings taken by spectrofluorometer with excitation at 490 nm and emission at >520 nm for the next 30 minutes in 1 to 2 minute intervals.

TABLE 3

Buffer Recipes for the SNAPtide ™ Assay Components

| Buffer | 1M HEPES | $ZnCl_2$ | 1M DTT | BSA | Tween 20 | Nuclease Free Water* |
|---|---|---|---|---|---|---|
| A | 2 mL | 4 mg | 500 μL | 100 mg | 0 | 97.5 mL |
| B | 2 mL | 4 mg | 125 μL | 0 | 100 μL | 97.775 mL |

Abbreviations:
DTT = dithiothreitol,
BSA = bovine serum albumin.

Example 4

Aptamer-3'-Fc or Aptamer-3'-C3b Conjugate

If aptamers are conjugated at their 3' end to the Fc fragment of IgG antibodies or the C3b component of complement, they could conceivably be used to opsonize encapsulated bacteria. To test this contention, tosyl-MBs (Dynal Corp.) were conjugated to poly-D-glutamic acid (PDGA) as previously described by Bruno and Kiel (2002). PDGA is the major component of the capsule of *Bacillus anthracis* (anthrax) pathogenic strains, which enables the vegetative cells to escape phagocytosis. PDGA-conjugated MBs were used to emulate vegetative anthrax bacteria and determine if aptamer-3'-Fc conjugates could enhance the phagocytosis of PDGA-MBs and by inference, opsonize encapsulated bacteria. The following describes the protocols used in these experiments.

RAW264.7 murine macrophages were split by scraping and add $10^5$ cells into each well of a sterile six-well culture plate using fresh RPMI-1640 cell culture medium plus 10% fetal bovine serum (FBS). In practice, 1 mL of cell suspension was used with 4 mL of fresh RPMI-1640 plus 10% FBS. The plate sat overnight to allow the cells to attach.

Five different tubes were labeled per Table 4 as follows (all volumes in μL):

TABLE 4

| Tube Contents | | | | | |
|---|---|---|---|---|---|
| Rd 5 Apt* | — | — | 20 | — | — |
| Fc-Apt* | — | — | — | 20 | 20 |
| 2XBB | 50 | 50 | 30 | 30 | 30 |
| Final Volume | 60 | 60 | 60 | 60 | 60 |

*Note:
Round 5 aptamer heated at 95° C. for 5 minutes prior to adding to tube;
Apt. = aptamer, Fc-Apt conjugate heated at 65° C. for 5 minutes prior to adding to tube. Heating is performed to ensure single-strandedness of the aptamers before they bind PDGA.
2XBB = 2X aptamer binding buffer (Bruno and Kiel, 2002).

Each tube was incubated for 30 minutes at RT to allow binding of any aptamers or aptamer-Fc conjugates with PDGA-MBs or other targets to occur Tube contents were loaded to the appropriate wells of a 6-well plate, and incubated at 37° C. and 5% $CO_2$ and then counted at 1, 2, and 24 hours using an inverted microscope.

Data were evaluated using a "phagocytic index" parameter. The formula used for the phagocytic index according to Welkos et al., 2001 was:

Phagocytic Index=Mean number of MBs/cell $X$ % of cells with at least one MB

Table 5 summarizes the raw data from the opsonization studies, as well as the phagocytic indices, which were derived from the above equation using the raw data. The controls that appeared to show enhanced phagocytosis may be due to some nonspecific binding of the aptamers to other targets or the innate ability of macrophages to recognize certain types of foreign matter (MBs or coated MBs). It also appears from Table 5 that there was some dose-dependence to the Fc-aptamer enhancement because in the first experiment the percentage of cells showing phagocytosis jumped from 74.67% to 96% with an increased level of Fc-aptamer conjugate (see highlighted data in Table 5).

TABLE 5

Raw Data and Phagocytic Indices for All Macrophage Studies in Phase I

Macrophage Test No. 1: 24 hr. Count

| Well | # of cells counted | # w/o MB association | # of MB | Mean # of MB per Cell | % cell w/ MB | Phagocytic Index |
|---|---|---|---|---|---|---|
| Blank (2XBB) | 300 | 300 | 0 | 0 | 0.00% | 0.00 |
| 5 uL Tosyl-MBs | 300 | 138 | 416 | 1.39 | 54.00% | 0.75 |
| 50 uL PDGA-MB + FcApt | 300 | 12 | 586 | 1.95 | 96.00% | 1.88 |
| 5 uL PDGA + FcApt | 300 | 76 | 402 | 1.34 | 74.67% | 1.00 |

Macrophage Test No 2: 1 hr. Count

| Well (total volume added 30 uL) | # of cells counted | # w/o MB association | # of MB | Mean # of MB per Cell | % cell w/ MB | Phagocytic Index |
|---|---|---|---|---|---|---|

TABLE 5-continued

Raw Data and Phagocytic Indices for All Macrophage Studies in Phase I

| | | | | | | |
|---|---|---|---|---|---|---|
| Blank (2XBB) | 300 | 300 | 0 | 0 | 0.00% | 0.00 |
| Tosyl-MBs | 300 | 273 | 52 | 0.17333333 | 9.00% | 0.02 |
| PDGA-MBs | 300 | 272 | 67 | 0.22 | 9.33% | 0.02 |
| Tosyl + FcApt | 300 | 218 | 139 | 0.46 | 27.33% | 0.13 |
| PDGA + FcApt | 300 | 187 | 243 | 0.81 | 37.67% | 0.31 |

Macrophage Test No. 3: 1 hr. Count

| Well (total volume added 60 uL) | # of cells counted | # w/o MB association | # of MB | Mean # of MB per Cell | % cell w/ MB | Phagocytic Index |
|---|---|---|---|---|---|---|
| Blank | 300 | 300 | 0 | 0.00 | 0.00% | 0.00 |
| 2-Tosyl | 300 | 246 | 83 | 0.28 | 18.00% | 0.05 |
| 3-PDGA | 300 | 246 | 116 | 0.39 | 18.00% | 0.07 |
| Tosyl + FcApt | 300 | 252 | 116 | 0.39 | 16.00% | 0.06 |
| PDGA + FcApt | 300 | 206 | 195 | 0.65 | 31.33% | 0.20 |

Macrophage Test No. 3: 2 hr. count

| Well (total volume added 60 uL) | # of cells counted | # w/o MB association | # of MB | Mean # of MB per Cell | % cell w/ MB | Phagocytic Index |
|---|---|---|---|---|---|---|
| Blank (2XBB) | 300 | 300 | 0 | 0.00 | 0.00% | 0.00 |
| Tosyl | 300 | 186 | 512 | 1.71 | 38.00% | 0.65 |
| PDGA | 300 | 158 | 256 | 0.85 | 47.33% | 0.40 |
| Tosyl + FcApt | 300 | 212 | 264 | 0.88 | 29.33% | 0.26 |
| PDGA + FcApt | 300 | 136 | 498 | 1.66 | 54.67% | 0.91 |

Macrophage Test No. 3: 24 hr. count

| Well (total volume added 60 uL) | # of cells counted | # w/o MB association | # of MB | Mean # of MB per Cell | % cell w/ MB | Phagocytic Index |
|---|---|---|---|---|---|---|
| Blank (2XBB) | 300 | 300 | 0 | 0.00 | 0.00% | 0.00 |
| Tosyl-MB | 300 | 44 | 676 | 2.25 | 85.33% | 1.92 |
| PDGA-MB | 300 | 53 | 628 | 2.09 | 82.33% | 1.72 |
| Tosyl + FcApt | 300 | 92 | 854 | 2.85 | 69.33% | 1.97 |
| PDGA + FcApt | 300 | 52 | 804 | 2.68 | 82.67% | 2.22 |

Each of these references is incorporated by reference in its entirety:

U.S. Pat. No. 5,270,163 et seq., U.S. Pat. No. 5,475,096, U.S. Pat. No. 6,566,343, U.S. Pat. No. 6,623,926.

Bell et al., "Oligonucleotide NX1838 Inhibits VEGF165-Mediated Cellular Responses In Vitro," *In Vitro Cell Develop. Biol. Animal.* 35:533-542 (1999).

Bruno, "In Vitro Selection of DNA to Chloroaromatics Using Magnetic Microbead-Based Affinity Separation and Fluorescence Detection," *Biochem. Biophys. Res. Comm.* 234: 117-120(1997).

Bruno and Kiel, "Use of Magnetic Beads in Selection and Detection of Biotoxin Aptamers by ECL and Enzymatic Methods," *BioTechniques.* 32:178-183 (2002).

Dougan et al., "Extending the Lifetime of Anticoagulant Oligodeoxynucleotide Aptamers in Blood," *Nuclear Med. Biol.* 27:289-297 (2000).

Murphy et al., "An improved method for the in vitro evolution of aptamers and applications in protein detection and purification." *Nucleic Acids Res.* 31:e110-e118 (2003).

Ono et al., "2'-Fluoro modified nucleic acids: polymerase-directed synthesis, properties and stability to analysis by matrix assisted laser desorption/ionization mass spectrometry," *Nucl. Acids Res.* 25:4581-4588 (1997).

Ulrich et al., "In Vitro Selection of RNA Aptamers that Bind the Cell Adhesion Receptors of *Trypanosoma cruzi* and inhibit cell invasion," *J. Biol. Chem.* 277:20756-20762 (2002).

Welkos et al., "The Role of antibodies to *Bacillus anthracis* and anthrax toxin components in inhibiting the early stages of infection of anthrax spores." *Microbiology.* 147:1677-1685 (2001).

What is claimed is:

1. A polymerase chain reaction (PCR)-based method of preparing a therapeutically effective amount of a DNA-3'-protein conjugate comprising:
   a) preparing through PCR a ds-DNA with a 3' overhang of adenine (A), cytosine (C), or guanine (G) deoxynucleotides on a ss-DNA strand of interest;
   b) coupling the ss-DNA's primary aryl amine of the 3' overhang to a protein conjugate via a biocompatible bifunctional linker; and
   c) separating the ds DNA into ss DNA and ss-DNA-3'-protein conjugate and purifying the ss DNA-3'-protein conjugate for therapeutic use, or optionally
   d) purifying the ds-DNA-3'-protein conjugate for therapeutic use.

2. The method of claim 1, wherein said 3' overhang is added to said ds-DNA by two rounds of amplification.

3. The method of claim 1, wherein said 3' overhang is added to said ds-DNA by terminal deoxynucleotide transferase (TdT).

4. The method of claim 1, wherein the ds-DNA is an aptamer.

* * * * *